(12) United States Patent
Wohrle

(10) Patent No.: US 6,619,559 B2
(45) Date of Patent: Sep. 16, 2003

(54) SCENT DELIVERY SYSTEM

(76) Inventor: Gregory D. Wohrle, 1110 Cherry Palm La., Hollywood, FL (US) 33019

( * ) Notice: Subject to any disclaimer, the term of this patent is extended or adjusted under 35 U.S.C. 154(b) by 0 days.

(21) Appl. No.: 09/902,307

(22) Filed: Jul. 10, 2001

(65) Prior Publication Data

US 2002/0048530 A1 Apr. 25, 2002

Related U.S. Application Data

(60) Provisional application No. 60/217,161, filed on Jul. 10, 2000.

(51) Int. Cl.$^7$ ................................................ A24F 25/00
(52) U.S. Cl. .......................................... 239/34; 239/53
(58) Field of Search ........................ 239/34, 53, 57–59; 261/30, DIG. 65

(56) References Cited

U.S. PATENT DOCUMENTS

| | | |
|---|---|---|
| 2,103,609 A | 12/1937 | Bradburn |
| 4,603,030 A | 7/1986 | McCarthy |
| 4,629,604 A | 12/1986 | Spector |
| 4,905,112 A | 2/1990 | Rhodes |
| 5,023,020 A | 6/1991 | Machida et al. |
| 5,071,621 A | 12/1991 | Tokuhiro et al. |
| 5,115,976 A | 5/1992 | Weiss et al. |
| 5,178,327 A | 1/1993 | Palamand et al. |
| 5,431,885 A | 7/1995 | Zlotnik et al. |
| 5,591,409 A | 1/1997 | Watkins |
| 5,695,692 A | 12/1997 | Kennedy |
| 5,724,256 A | 3/1998 | Lee et al. |
| 5,832,320 A | 11/1998 | Wittek |
| 5,919,418 A | 7/1999 | Kendall et al. |
| 5,972,290 A | 10/1999 | De Sousa |

Primary Examiner—Lisa A. Douglas
(74) Attorney, Agent, or Firm—Gold & Rizvi, P.A.; Glenn E. Gold; H. John Rizvi

(57) ABSTRACT

An electronic scent-delivery system (10) is provided having one or more cartridges (100) filled with scented oil and maintained within pockets (53) of a tray (50) slidable within a tray support member (40) of a housing (20,30,60). Heating elements (76) are provided for indirectly heating the scented oil to an evaporative state, and acutating apparatus (92) are provided for engaging the cartridges to enable the scented evaporate to escape the cartridges. A blowing apparatus (86) provides an airflow over the tops of the cartridges, thereby directing the scented evaporate out of the housing through vents (65) in the housing faceplate (60) and into the surrounding environment.

14 Claims, 4 Drawing Sheets

SCENT DELIVERY SYSTEM

CROSS-REFERENCE TO RELATED APPLICATIONS

This application claims the benefit of U.S. Provisional Patent Application Ser. No. 60/217,161 filed on Jul. 10, 2000.

BACKGROUND OF THE INVENTION

1. Field of the Invention

The present invention relates generally to scent diffusing devices, and more particularly to a personal electronic scent diffusing system.

2. Description of the Prior Art

It is well known to use deodorizers, air fresheners and the like, to provide a desired scent or aroma in a home environment. In fact, many people place air fresheners in a room to cover up odors in the room or just to add a fragrant scent to the air. Many air fresheners are commercially available. However, most of these provide for only a single scent having a fixed strength.

Some air fresheners which allow a user to selectively alter the scent delivered by a device have been described. For example, U.S. Pat. No. 5,695,692 to Kennedy and U.S. Pat. No. 5,178,327 to Palamand disclose air freshening units including a container which carries a cartridge having a plurality of segments, or sections, each having a solid material impregnated with a scented substance. In each case, the cartridge can be manually rotated to position a particular segment having a desired scent into alignment with an opening in the container to emit the desired scent.

U.S. Pat. No. 2,103,609 to Bradburn discloses an air freshener having a body which carries a plurality of open topped vials of scented substances. A cover is rotatably mounted on the body to seal and close the vials. The cover has an opening which can be selectively brought into alignment with any one of the vials to open the vial, to allow the substance within the vial to evaporate and freshen the air.

The aforementioned air fresheners share a number of disadvantages and limitations. First, each of the disclosed air fresheners must be manually manipulated to alter the scent. Second, none of the disclosed air fresheners provide a means for controlling the strength or duration of the scent. Third, the disclosed air fresheners are provided in containers which would be unsightly positioned in a high-end home entertainment unit.

Electronic aroma generating devices and systems have been described which provide for more controlled scent emission. For example, U.S. Pat. No. 5,591,409 to Watkins discloses an apparatus for introducing precisely controlled amounts of aromatic chemicals, using metered spray technology, into the immediate vicinity of the operator. The disclosed mechanism is particularly oriented toward use by an individual sitting at a desk using a microcomputer. Similarly, U.S. Pat. No. 5,724,256 to Lee et al. discloses a computer controlled odor mixing and dispensing system suitable for use in conjunction with a multimedia computer application. Neither of these systems are designed for, nor suitable for, providing an aroma to a larger area such as one or more rooms of a home.

U.S. Pat. No. 4,603,030 to McCarthy, U.S. Pat. No. 5,832,320 to Wittek, and U.S. Pat. No. 5,972,290 to De Sousa each describe scent emitting systems designed to provide a variety of different scents to intensify sensorial perception of an audience in attendance of a visual and/or acoustical representation, by introducing scents in synchronism with the visual and/or acoustic representation. However, the aforementioned systems are complex, expensive and adapted for emitting scents over a large area such as a movie theater.

Accordingly, there is an existing need for an electronic scent emitting system particularly suited for use in a home environment which overcomes the aforementioned disadvantages and limitations of the prior art systems.

DETAILED DESCRIPTION OF THE PREFERRED EMBODIMENTS

Figure 1:
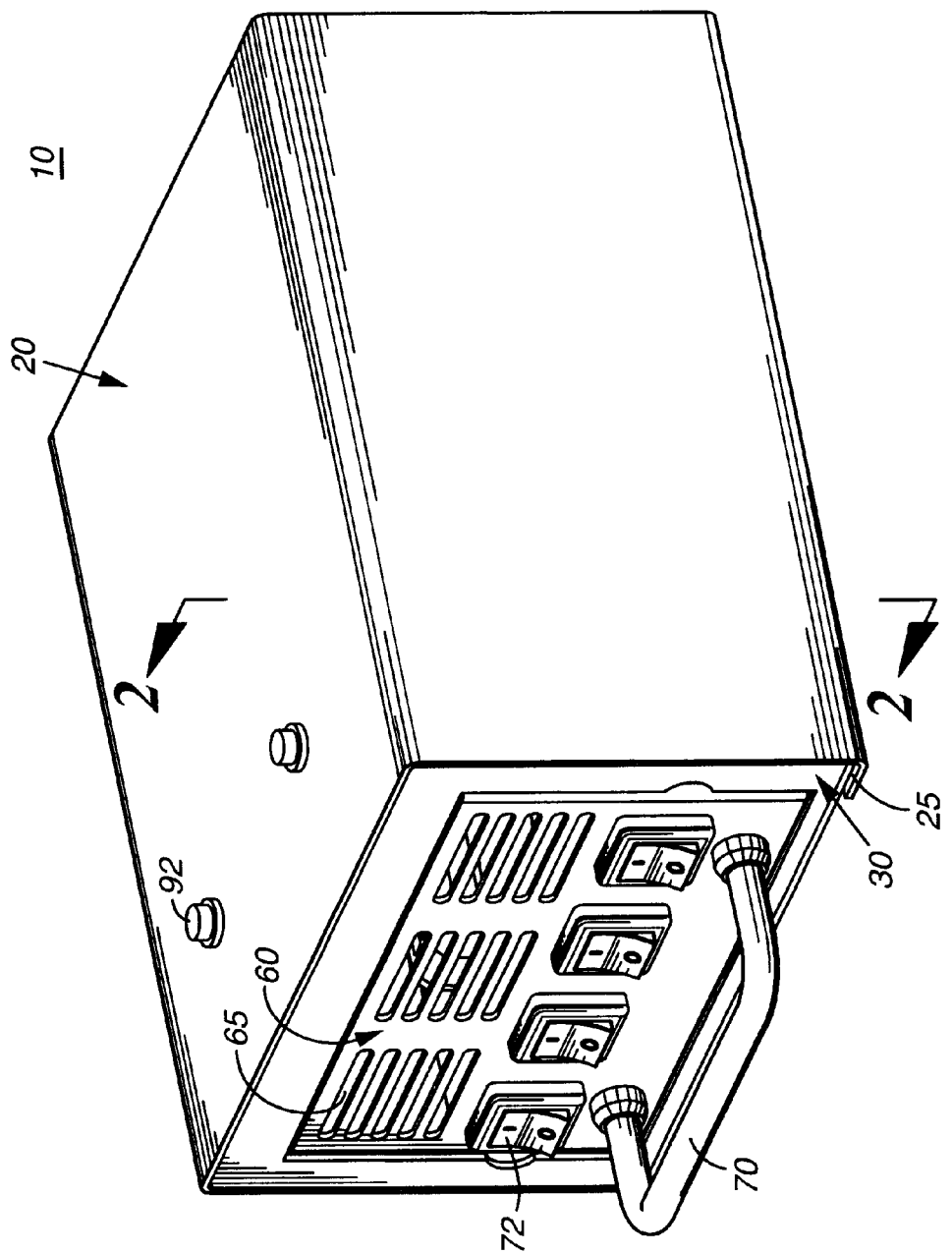
FIG. 1 is perspective view of the scent delivery system of the present invention in a completely assembled state.

Referring now to FIG. 1, the portable electronic scent delivery system of the present invention is shown generally as reference numeral 10. In this fully assembled state, the system has a relatively compact, lightweight structure and approximates the size of a small stereo system component. The major components of the system are contained within a housing, including an upper housing member 20, a lower housing member 30 and a front face plate 60. The front face plate 60 includes a plurality of electronic switches 72 disposed therethrough for controlling power to the unit, as well as various other electronic functions described in more detail below. Generally, scents emitted from one or more cartridges (not shown in FIG. 1) housed within the system are directed outwardly through vents 65 in the faceplate 60 by a blowing means (not shown in FIG. 1).

Figure 2:
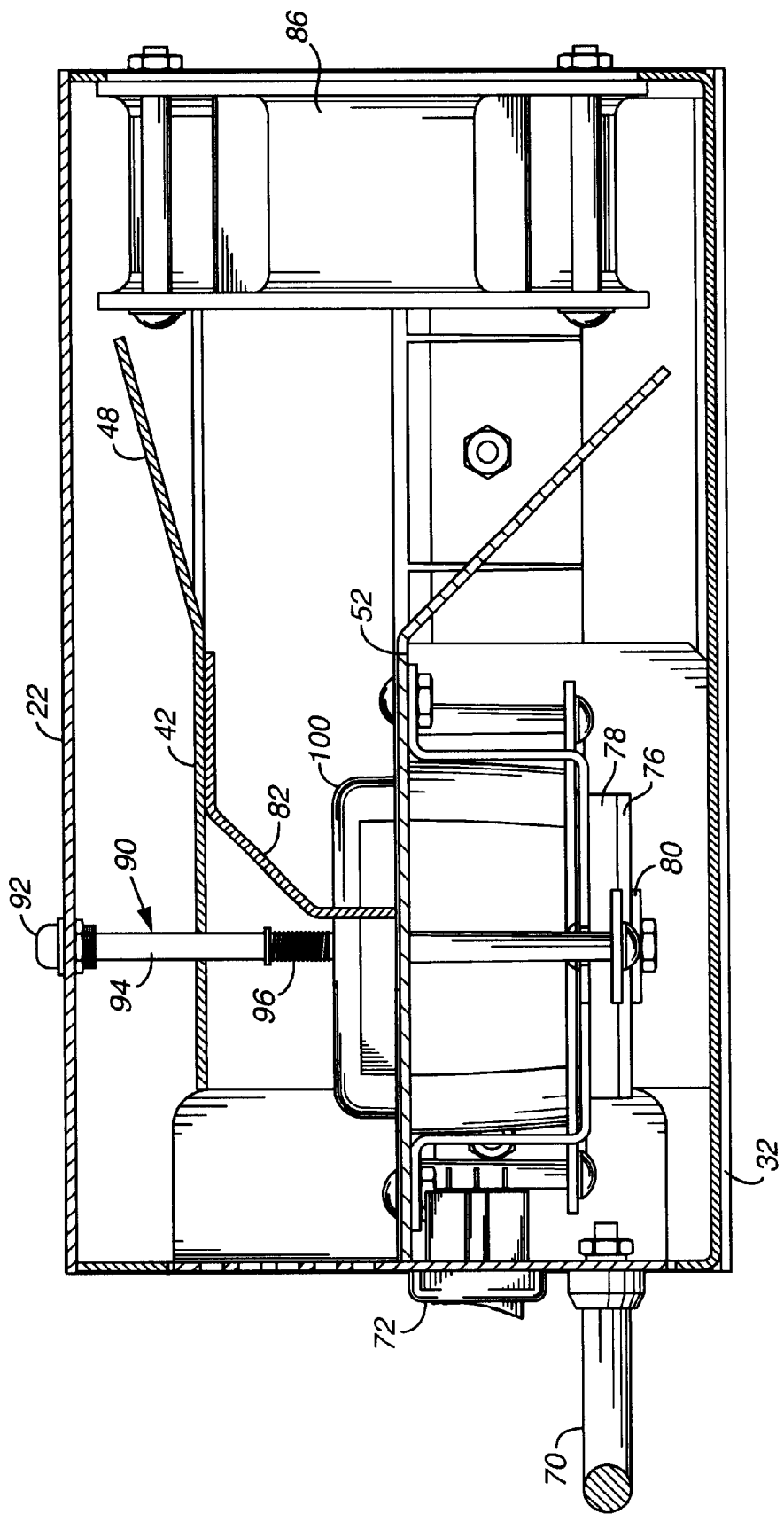
FIG. 2 is a cross-sectional view of line 2—2 of FIG. 1.
Figure 3:
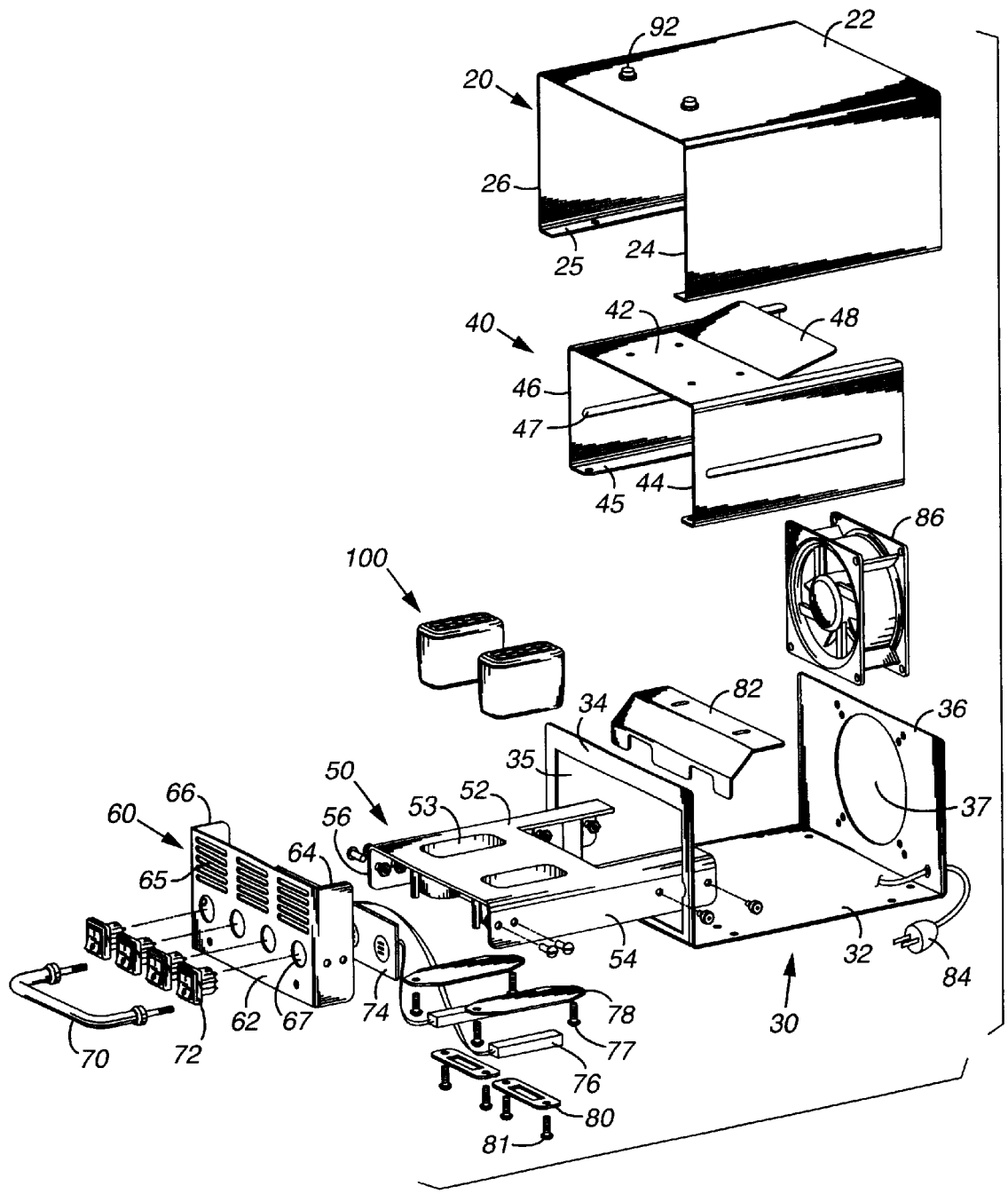
FIG. 3 is an exploded perspective view of the scent delivery system of the present invention.

Referring now particularly to FIGS. 2 and 3, the major components of the system will be described in more detail. Upper housing member 20 includes a top side 22 joining opposite side walls 24 and 26. Longitudinal support rails 25 depend inwardly from the lower ends of side walls 24 and 26. Lower housing member 30 includes a base 32 having upwardly depending front and rear sides 34 and 36. Front side 34 has an opening 35 sized and shaped for enabling front face plate 60 to be slidably received therethrough. Rear side 36 has an opening 37 provided therethrough for enabling air to be drawn into blower fan 86 attached to its inner surface. Upper and lower housing portions, 20 and 30, are preferably joined by conventional mechanical fasteners extending through aligned apertures in rails 25 and base 32.

A tray support member, shown generally as reference numeral 40, includes a top side 42 joining opposite side walls 44 and 46. A rear portion of top side 42 slopes upwardly to create an integral baffle portion 48 for directing airflow from blower 86 toward face plate vents 65. The lower ends of side walls 44 and 46 depend inwardly to form lower tray support rails 45. Tray support rails 45 rest upon longitudinal support rails 25 of upper housing portion 20 and are fastened thereto by conventional mechanical fastening means. The inner surfaces of side walls 44 and 46 further include longitudinally extending upper tray guide rails 47. Preferably, tray support member 40 has a unitary molded plastic construction.

A tray member, shown generally as reference numeral 50, includes a top side 52 and opposite side walls 54 and 56. Top side 52 has integral pockets 53 sized and shaped for snugly receiving scent cartridges 100 therein. When fully assembled, tray member 50 is slidably received within tray supporting member 40. More specifically, the lower edges of sides 54 and 56 slide along the upper surfaces of tray support rails 45, and the upper surface of top side 52 slidably engages upper tray guide rails 47. Sides walls 54 and 56 of tray member 50 are fastened to respective sides 64 and 66 of front face plate 60. Consequently, tray member 50 can be slidably opened by manually pulling on handle member 70.

Heating subassemblies are provided for heating the bottoms surfaces (not shown) of integral cartridge-receiving pockets 53. Each heating subassembly includes a thermally conductive plate member 78 interposed between a heating element 76 and the bottoms surface of a cartridge-receiving pocket 53. The heating subassemblies are maintained in place by mechanical retainers 80 and corresponding fasteners 81 attached directly to the bottom of tray 50.

Main power to the system and the associated electronic components is preferably provided using electricity supplied by a standard 110 or 220 Volt AC power source through a conventional electrical plug 84. A plurality of electrical switches 72 are provided for controlling various functions of the system via circuitry provided on a printed circuit board 74. Preferably, the system includes switches for controlling main power to the unit, as well as controlling blower speed and actuation of the heating elements 76.

Figure 4:
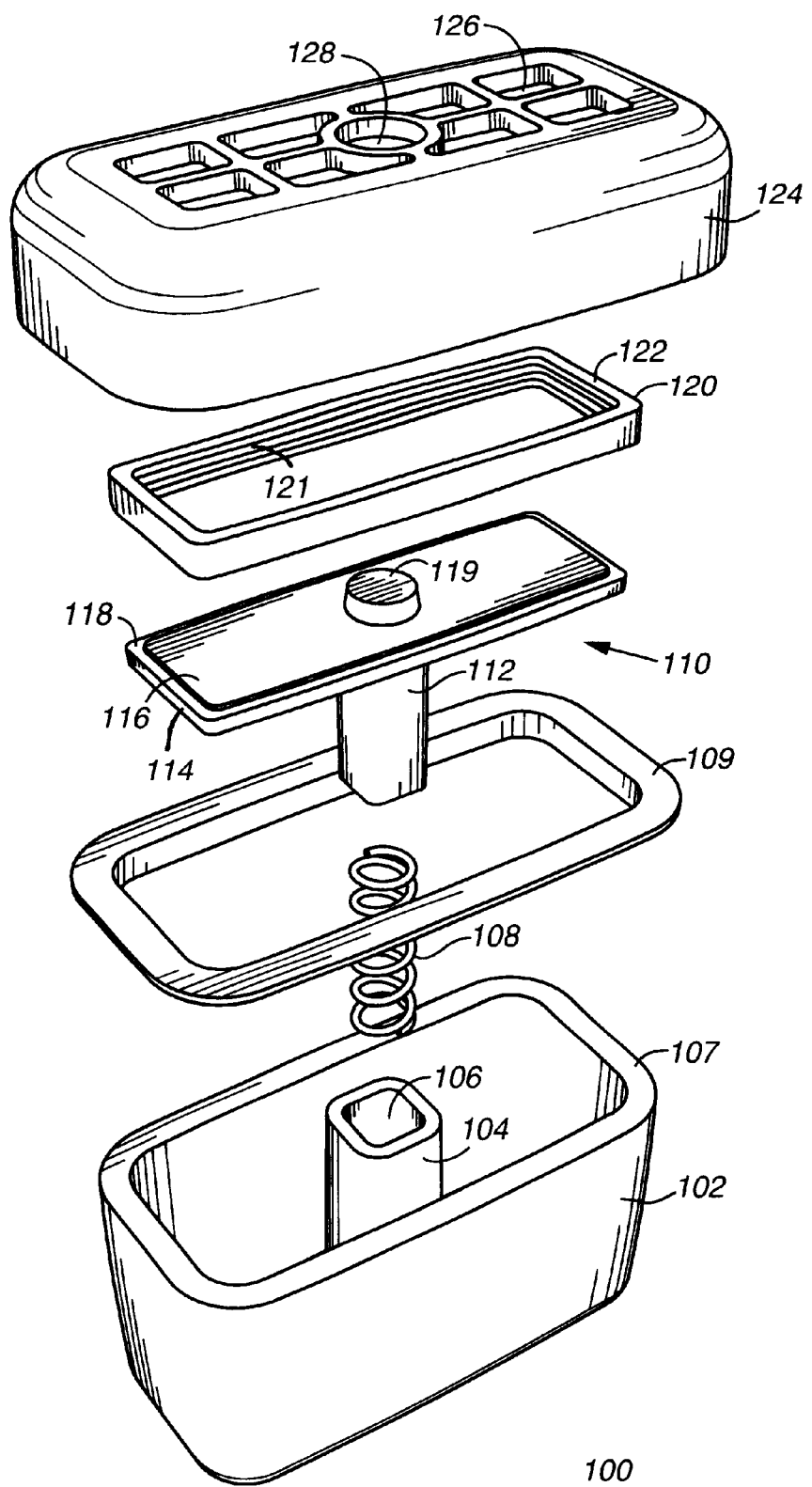
FIG. 4 is an exploded view of cartridge 100.

Referring now specifically to FIG. 4, each scent cartridge 100 includes a lower housing body 102 and an upper housing cap 124 separated by a sealing gasket member 109 interposed therebetween. Lower housing body 102 includes an integral upwardly extending body 104 defining a channel 106. The lower housing body 102 and upper housing cap 124 are preferably constructed from a high-melting temperature polymer. Preferably, the housing is optically transparent, enabling a system operator to periodically check the cartridge oil levels for replacement.

A plastic molded T-shaped member, shown generally as reference numeral 110, includes a base 114 having an integral body 112 depending downwardly therefrom and defining a spring-receiving channel (not shown) therein. The outer surface of body 112 is sized and shaped for enabling body 112 to be snugly received within channel 106. Compression spring 108 is received at its upper end within body 112 such that, when fully inserted within body 112, the lower end of spring 108 extends beyond the lower end of body 112. In this manner, when body 112 is received within channel 106, the spring 108 acts to bias T-shaped member 110 in an upward direction. Base 114 has a raised upper surface portion 116 defining a peripheral base portion 118. Furthermore, raised surface portion 116 has a centrally positioned nub 119 protruding upwardly therefrom.

Gasket member 120 is provided having a continuous groove 121 extending about its inner surface sized and shaped for being sealingly fitted about peripheral base portion 118 of T-shaped member 110. Upper housing cap 124 includes a plurality of window apertures 126 and a centrally positioned aperture 128 sized and shaped for receiving nub 119 therethrough. Lower housing body is filled with a volume of scented oil (not shown), preferably having a level below the upper end of body 104. When the cartridge is fully assembled, the cartridge compression spring 108 biases the T-member upwardly such that gasket 120 forms an air tight seal again the inner surface of housing cap 124 exterior to the apertures 126, 128 provided therein. Furthermore, nub 119 preferably extends at least partially through aperture 128.

Referring now to FIGS. 2–4, and primarily to FIG. 2, at least one actuating mechanism, shown generally as reference numeral 90, is provided above each oil filled cartridge 100, for selectively biasing cartridge nub 119 downwardly to break the seal between upper surface 122 of gasket 120 and the inner surface of housing cap 124. In the accompanying FIG. 2, a manual actuating mechanism operating substantially similar to that of a conventional ball point pen is shown. However, it will be apparent to those skilled in the art that myriad different types of manual, as well as automatic, actuating means could be employed.

The operation of the scent diffusing system of the present invention will now be described in more detail. As best depicted in FIGS. 1–3, the system includes a plurality of control buttons 72 for enabling a system user to perform a variety of functions, including, but not limited to: (1) turning the system on and off; (2) activating a particular heating element, thereby activating a particular cartridge; and (3) controlling the speed of the blowing mechanism 86. Although the accompanying drawing figures illustrate a two-cartridge arrangement, the invention is not intended to be so limited. As will be apparent to those skilled in the art, the system of the present invention can be adapted to accommodate more or less cartridges.

The heat generated by heating element 76 is transferred, via thermally conducting plate member 78, through the bottom of tray pocket 53, to cartridge body 102. The temperature of heating member 126 is increased to a predetermined temperature range sufficiently high to cause the liquid scented oil to begin evaporating. At or about the same time the scented oil begins to evaporate, mechanism 90 is actuated via button 92 to depress T-shaped cartridge member 110, via contact with nub 119. In this manner, the air tight seal provided by gasket 120 is temporarily broken, enabling the scented evaporate to escape the cartridge through apertures 126 in cartridge cap 124. Blowing mechanism 86 provides an air flow over the tops of the cartridges 100, directing the scented evaporate through vents 65 in cover plate 60. Baffle members 48 and 82 aid in concentrating the flow of air toward the aforementioned vents 65.

While the preferred embodiments of the invention have been illustrated and described, it will be clear that the invention is not so limited. Numerous modifications, changes, variations, substitutions and equivalents will occur to those skilled in the art without departing from the spirit and scope of the present invention as described in the claims.

What is claimed is:

1. A scent-emitting cartridge for a scent-delivery system, the cartridge comprising:
    a housing defining an interior space adapted for containing a volume of liquid therein, said housing having at least one aperture extending through a side thereof; and
    means for selectively sealing said at least one aperture from said interior space, said sealing means positioned for being actuated through said at least one housing aperture between a sealed position and an unsealed position,
    wherein the release of a scent emitted from said liquid is controllably communicated through said at least one housing aperture to an exterior environment via the selective actuation of said sealing means.

2. A scent-emitting cartridge as recited in claim 1, wherein said selective sealing means further comprises an integrally formed member biased toward an interior surface of said housing to substantially prevent communication of a scent emitted from said liquid between said housing interior and said at least one aperture.

3. A scent-emitting cartridge as recited in claim 2, wherein said selective sealing means further comprises a biasing member urging said integrally formed member toward said housing interior surface.

4. A scent-emitting cartridge as recited in claim 3, wherein said biasing member further comprises a compression spring.

5. A scent-emitting cartridge as recited in claim 2, wherein said integrally formed member further comprises a substantially planar base portion positioned for being actuated toward an unsealed position through said at least one aperture, said planar base portion having upper and lower surfaces separated by a peripheral edge.

6. A scent-emitting cartridge as recited in claim 5, wherein said selective sealing means further comprises a gasket member disposed about said peripheral edge, said gasket member sized and shaped for forming a seal peripherally about said at least one aperture.

7. A scent-emitting cartridge as recited in claim 7, wherein said integrally formed member further comprises a leg portion depending downwardly from the lower surface of said planar base portion.

8. A scent-emitting cartridge as recited in claim 8, wherein said cartridge housing further comprises a raised wall portion extending upwardly from a lower interior surface thereof and defining a channel sized and shaped for slidably receiving the downwardly depending leg portion of said integrally formed member therein.

9. A scent-emitting cartridge for a scent-delivery system, the cartridge comprising:

an integrally molded lower housing portion generally defined by a base and a walled portion extending upwardly from the periphery thereof and terminating at an upper edge, the base having an interior walled portion rising vertically upward therefrom and defining a channel;

an integrally molded upper housing portion generally defined by a top side and a walled portion extending downwardly from the periphery thereof and terminating at a lower edge, the top side having at least one aperture extending therethrough, said upper and lower housing portions peripherally secured to each other about their respective edges;

an upwardly biased integrally formed member having a planar base portion terminating at a peripheral edge and a leg portion depending downwardly from a lower surface thereof, the leg portion sized and shaped for being slidably received within said channel, the upper surface of said planar base portion positioned for being actuated through said at least one aperture between a sealed position and an unsealed position; and a sealing member disposed about the peripheral edge of the planar base portion of said integrally formed member.

10. A scent-emitting cartridge as recited in claim 9, further comprising a biasing member for providing the upward bias of said integrally formed member.

11. A scent-emitting cartridge as recited in claim 10, wherein said biasing member further comprises a compression spring disposed within said channel between an upper surface of said lower housing base and a lower surface of the downwardly depending leg portion of said integrally formed member.

12. A scent-emitting cartridge as recited in claim 9, said upper and lower housing portions are secured to each other along their respective abutting peripheral edges by one of a chemical adhesive, a heat seal and a sonic weld.

13. A scent-emitting cartridge as recited in claim 9, wherein said upper and lower housing portions are secured to each other by mechanical fastening means.

14. A scent-emitting cartridge as recited in claim 9, wherein said upper and lower housing portions are secured to each other by integral snap fit means in the respective upper and lower housing portions.

* * * * *